United States Patent
Chang et al.

(10) Patent No.: US 6,924,387 B1
(45) Date of Patent: Aug. 2, 2005

(54) SOLID CATALYST WITH CORE-SHELL CATALYTIC PHASE AND A METHOD OF PREPARATION THEREOF

(75) Inventors: Tae-Sun Chang, Daejeon (KR); Deug-Hee Cho, Daejeon (KR); Dong-Koo Lee, Daejeon (KR); Guijia Li, Jilin (CN); Young Kil Lee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 09/622,200

(22) PCT Filed: Feb. 12, 1999

(86) PCT No.: PCT/KR99/00077

§ 371 (c)(1),
(2), (4) Date: Jan. 18, 2002

(87) PCT Pub. No.: WO99/41012

PCT Pub. Date: Aug. 19, 1999

(30) Foreign Application Priority Data

| Feb. 13, 1998 | (KR) | ............................................. 98-4340 |
| Mar. 31, 1998 | (KR) | ........................................... 98-11171 |
| May 15, 1998 | (KR) | ........................................... 98-17681 |
| Jul. 3, 1998 | (KR) | ........................................... 98-26820 |
| Aug. 10, 1998 | (KR) | ........................................... 98-32416 |
| Oct. 14, 1998 | (KR) | ........................................... 98-43076 |

(51) Int. Cl.$^7$ .................. C07C 253/00; B01J 21/00; B01J 23/00

(52) U.S. Cl. .................. 558/323; 558/319; 558/324; 502/249; 502/255; 502/311; 502/313; 502/314; 502/315; 502/316

(58) Field of Search .................. 502/104, 110, 502/113, 117, 205, 206, 212, 248, 249, 255, 311, 312, 313–316, 304, 322; 558/319, 323, 324

(56) References Cited

U.S. PATENT DOCUMENTS

| 4,212,766 A | * | 7/1980 | Brazdil et al. | ............... 502/205 |
| 4,292,203 A | * | 9/1981 | Milberger et al. | .......... 502/304 |
| 4,590,011 A | * | 5/1986 | Li | ............... 558/323 |
| 4,837,233 A | * | 6/1989 | Glaeser et al. | ............... 502/204 |
| 4,883,895 A | * | 11/1989 | Brazdil et al. | ............... 558/319 |
| 4,885,275 A | * | 12/1989 | Robison | ........................ 514/8 |
| 5,094,990 A | * | 3/1992 | Sasaki et al. | ................ 502/214 |
| 5,132,269 A | * | 7/1992 | Sasaki et al. | ................ 502/205 |
| 6,057,471 A | * | 5/2000 | Nakamura et al. | .......... 558/321 |

* cited by examiner

*Primary Examiner*—Cam N. Nguyen
(74) *Attorney, Agent, or Firm*—Greenblum & Bernstein, P.L.C.

(57) ABSTRACT

The present invention relates to a sold catalyst for manufacturing of a nitrile compound and a method of preparation thereof. More particularly, this invention relates to the solid catalyst expressed by the following formula (1): $Bi_aA_aB_bQ_qO_x$][(100-z) % $D_dE_eFe_fNi_gMo_mO_y$+z % $SiO_2$] comprising a core catalytic phase expressed by [(100-z)%=$D_dE_eFe_fNi_gMo_mO_y$+z % $SiO_2$] and a shell catalytic phase expressed by [$Bi_nA_aB_bQ_qO_x$], which increases a yield in the manufacturing of a nitrile compound via ammoxidation of olefin, and the method of preparation thereof.

5 Claims, No Drawings

SOLID CATALYST WITH CORE-SHELL CATALYTIC PHASE AND A METHOD OF PREPARATION THEREOF

BACKGROUND OF THE INVENTION

1. Field of the Invention

The present invention relates to a solid catalyst for manufacturing of a nitrile compound and a method of preparation thereof. More particularly, this invention relates to the solid catalyst expressed by the following formula (1), comprising a core catalytic phase expressed by [(100-z) $\%D_dE_eFe_fNi_gMo_mO_y$+z $\%$ $SiO_2$] and a shell catalytic phase expressed by [$Bi_nA_aB_bC_cO_x$], which increases a yield in the manufacturing of a nitrile compound via ammoxidation of olefin, and the method of preparation thereof:

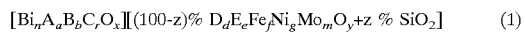

$[Bi_nA_aB_bC_cO_x][(100-z)\% \ D_dE_eFe_fNi_gMo_mO_y+z \% \ SiO_2]$ (1)

wherein A is one or more atoms selected from the group consisting of boron, phosphorus, molybdenum and arsenic;

B is one or more elements having the atomic valence of 1–2 selected the group consisting of potassium, cesium, nickel, cobalt, manganese and magnesium;

C is one or more elements having the atomic valence of 3–6 selected the group consisting of iron, chromium, cerium, niobium, vanadium and tellurium;

D is one or more elements having the atomic valence of 3–6 selected the group consisting of aluminum, cerium and chromium;

E is one or more elements having the atomic valence of 1–2 selected the group consisting of cobalt, manganese, magnesium, calcium, copper and cesium;

when m is 1, n is 0.001–3, a is 0.001–3, b is 0–3, c is 0–1, d is 0–3, e is 0–3, f is 0.015–5, g is 0.01–5, and z is 0–90; and x and y are numbers such that the valence requirements of the other elements for oxygen in the core and shell catalytic phase, respectively are satisfied.

2. Description of the Related Art

Acrylonitrile had been prepared via reaction of acetylene or ethylene oxide with HCN before a development of ammoxidation of propylene as raw materials. However, in light of the expensive raw materials employed therein, the problem of economics was apparent, and thus the new method was in need for the improvement thereof.

In addition, in the above process, propylene is oxidized to acrolein and is further oxidized to generate acrylic acid. The process has been recently applied to a manufacture of methacrylic acid and methacrylonitrile via methacrolein by using isobutylene as a reactant.

Acrylonitrile and acrolein have been widely used as a raw material for nitrile-based rubber, plastics, fibers and resin, and prepared by ammoxidation of propylene in the presence of multicomponent oxide catalyst.

About 50 years have passed since the procedure involving ammoxidation of olefin was first invented, and this procedure has been called an "allylic oxidations of lower olefins" up to now since its commercialization 35 years ago.

Now that the economical and industrial significance of such process involving ammoxidation of olefin, which is a catalytic reaction, has been recognized, the research on various aspects of the process have been intensively carried out.

The most noticeable changes have been made in the improvement of chemical compositions of the catalyst and the manufacturing method thereof, including the reaction process. Thanks much to the strenuous research thus far, a better yield of 80% to acrylonitrile in a commercial plant has been obtained, and more than 90% of the yield to acrylic acid in oxidation reaction has been achieved.

It has been reported that the active ingredients of some of the catalysts, which have been used in the commercial plant, are very complicated composite oxides comprising bismuth-molybdenum oxides or iron-antimony oxides as an essential component, together with a variety of additional atoms.

Among the conventional methods, the manufacturing methods of the catalyst, which is similar to the present invention or exhibits remarkable catalytic activity are explained as follows:

The German Patent No. 2,127,996 in 1972 (Ohorodnick, Alexander, etc.) disclosed a novel process of manufacturing acrylonitrile from propylene in the presence of a catalyst derived from Mo—Bi—Fe—P—O series, wherein a Mo—Bi—Fe—P—O catalyst having 58 $m^2/g$ of BET specific surface area was impregnated with $Fe(NO_3)_3$—$9H_2O$ to obtain a catalyst having 7.3 $m^2/g$ of specific surface area. The above patent disclosed that such catalyst had the following activity at the temperature of 470–485° C.: conversion was 91.0%, and selectivity was 75.2% to acrylonitrile.

According to the U.S. Pat. No. 4,052,332 in 1977 (du Pont de Nemours, E.I., and Co.) designed to regenerate a Bi—Mo—P—K—Co—Ni—Si—O catalyst after use, it disclosed that a solution containing $MoO_3$, $H_3PO_4$, $HNO_3$, and $Bi(NO_3)_3$ $5H_2O$, $H_2O$ was impregnated with a catalyst for the purposes of the regeneration. Consequently such catalyst may be reused for the manufacture of acrylonitrile from propylene.

The U.K. Patent No. 1,518,215 in 1978 (Societa Italiana Resine S.p.A) disclosed the process, wherein, to a $(NH_4)_6Mo_7O_{24}$ solution, hydrochloric acid was added, and with further addition of $Fe(NO_3)_3 9H_2O$ solution, the mixture was dried, pulverized and calcined. Then, $Bi(NO_3)_3 5H_2O$ solution was sprayed to the residue, dried and calcined repeatedly to obtain the catalyst. It was reported that acrylonitrile with about 70% of selectivity was obtained at the temperature of 455° C.

Standard Oil Co. of U.S.A. reported the process in which $Bi(NO_3)_3$ $5H_2O$ solution was mixed with $(NH_4)_6Mo_7O_{24}$ solution in one reactor to obtain solution A with adjustment of pH. Then, solution B containing $KNO_2$, $Ni(NO_3)_3$ $6H_2O$, $Co(NO_3)_2$ $6H_2O$, and $Fe(NO_3)_3$ $9H_2O$ in another reactor was prepared. Further, $H_3PO_4$ and silica sol were mixed in another reactor, after which solution A was added to the mixture, followed by the addition of solution B. Then, the mixed solution was dried, calcined and pulverized. The typical catalyst included $[50\%][Bi_2Mo_3O_{12}]\frac{1}{2}[K_{01}Ni_{25}Co_{45}Fe_fP_{0.5}Mo_mO_2H+50\%$ $SiO_2]$ based on the method herein. The portion of such catalyst was assumed that it was composed of two phases, namely a key catalytic phase and a host-catalyst phase. But this terminology is used for descriptive purposes only because they were actually not composed of a simple mixture. Such catalyst was characterized in that the yield of both acrylonitrile and HCN were increased while the consumption of ammonia was reduced (U.S. Pat. No. 1,212,766).

In addition, Standard Oil Co. of U.S.A. reported the process using a catalyst comprising a composite oxide consisting of Mo, Fe and Bi, and atoms in the groups of 1A, 2A, 3A, 4A and 5A in the periodic table, which was prepared by impregnating potassium with a solution of potassium acetate. The yield of 80% to acrylonitrile was obtained at 430° C. in the presence of such catalyst, and in particular, the impregnating catalyst was superior to that of the conventional non-impregnating catalysts in terms of yields (Japanese Unexamined Publications Sho 83-143,842 and U.S. Pat. No. 4,144,134).

Nitto Chemical Industry Co. of Japan disclosed a process of manufacturing a catalyst derived from Mo—Bi—Fe—Ni—Si—O in such a manner that a slurry or dispersed solution consisting of Mo and Fe was prepared by the adjustment of pH. While heating the solution, other components were added therein, followed by spray-drying or thermal treatment to obtain a fluidized bed catalyst. The final product had the following characteristics in the presence of such catalyst at 450° C.: conversion of propylene was 98.8%, and selectivity was 83.2% to acrylonitrile (Japanese Patent No. 89,265,067).

The Standard Oil Co. of U.S.A. disclosed a catalyst for ammoxidation containing the following active ingredients an oxide of Mo, Bi, Fe, Co, Ni and Cr, and P, Sb, alkali, metals, alkaline earth metals, or rare earth metals (U.S. Pat. No. 5,134,105).

Technische Hochschule Carl Schorlemmer Leuna-Merseburgh Co. of Germany reported a method of manufacturing a catalyst in such a manner that $Bi(NO_3)_3 5H_2O$ was impregnated with an oxide consisting of Bi, Mo, Cr, Fe, Co, Na, and Si, thereby enhancing the selectivity thereof (German Patent No. 4,124,666 and No. 4,200,006).

In addition to the above cited patents, many researchers have conducted and intensive studies have been made on such catalysts.

Burkhardt, I. et al. of Germany reported that in line with the method of manufacturing a $Fe_2O_3MoO_3/SiO_2$ catalyst, the acidity was changed with the addition of Fe in the $MoO_3/SiO_2$ catalyst depending on the nature of oxidation and reduction. The research on the activity of ammonia on catalyst was carried out by infrared spectrophotometer (React. Kinet. Catal. Lett. 1987, 34(2), 309–15).

Kripylo, Peter, et al. of Germany carried out a research on the topic of the relationship between the structure and activity with respect to the Bi—Mo multicomponent oxides. It was reported that the active phase in the Bi—Mo catalyst had a structure comprising Fe, Co and Cr ions between the layer of $MoO_3$. The ions were of significance to the formation of the active phase. Further, if the contents of Bi increased, the selectivity of acrylonitrile was further enhanced in proportion thereto (Chem. Tech. 1991, 43(3), 116–20).

In addition, Caldararu, H et al. studied the site of $Fe^{34}$ ion relating to $Bi_2FeMo_2O_{12}$ and $Bi_2Fe_2Mo_2O_{12}$ having a schcelite structure so as to observe the changes in the catalytic activity depending on the structure thereof. For example, the $Fe^{34}$ ion in $Bi_2FeMo_2O_{12}$ having tetragonal or monoclinic form was located on the tetrahedral site, and this location was not affected by reduction (Z. Phys. Chem. 1992, 177(1), 75–92).

Mehner, H. et al. reported that according to the surface analysis and transmission electron microscopy, the active phase relating to the reaction in a catalyst derived from a multicomposite molybdenum oxides was not present on the surface. Further, it was reported that all of components were participated in the reaction therein (Mater. Sci. Eng., B 1994, 25(1), 1–4).

As explained above, much research for the better catalytic activity has been made in various aspects of the catalyst.

SUMMARY OF THE INVENTION

It has been reported that a catalyst of $Bi_2O_3$—$MoO_3$ system during ammoxidation exhibits a high catalytic activity and is prepared by a slurry technique.

According to this invention, the core catalytic phase containing molybdenum, iron, nickel, D and E as main component is prepared by the slurry technique, followed by calcination at certain temperature, and the shell catalytic phase containing, bismuth, A, B and C as main component is then prepared by a impregnation technique using the core catalytic phase as support.

The solid catalyst so obtained has better function, although the amount of high-priced bismuth is minimized and consequently led to economical merits.

Therefore, an objective of this invention is to provide a solid catalyst comprising the core catalytic phase and the shell catalytic phase, which is superior to catalyst prepared by the conventional method in terms of catalytic activity and production cost.

DETAILED DESCRIPTION OF THE INVENTION

This invention is characterized by a solid catalyst with a core catalytic phase and a shell catalytic phase expressed by the following chemical formula (1).

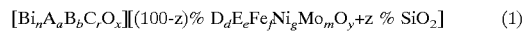

$$[Bi_nA_aB_bC_cO_x][(100-z)\% \ D_dE_eFe_fNi_gMo_mO_y+z \% \ SiO_2] \quad (1)$$

wherein A is one or more atoms selected from the group consisting of boron, phosphorus, molybdenum and arsenic;

B is one or more elements having the atomic valence of 1–2 selected the group consisting of potassium, cesium, nickel, cobalt, manganese and magnesium;

C is one or more elements having the atomic valence of 3–6 selected the group consisting of iron, chromium, cerium, niobium, vanadium and tellurium;

D is one or more elements having the atomic valence of 3–6 selected the group consisting of aluminum, cerium and chromium;

E is one or more elements having the atomic valence of 1–2 selected the group consisting of cobalt, manganese, calcium, copper and cesium;

when m is 1, n is 0.001–3, a is 0.001–3, b is 0–3, c is 0–1, d is 0–3, e is 0–3, f is 0.01–5, g is 0.01–5, and z is 0–90; and x and y are numbers that the valence requirements of the other elements for oxygen in the core and shell catalytic phase, respectively are satisfied.

This invention is also characterized by a process of preparing a solid catalyst expressed by the above formula (1), which comprises the steps of:

(a) forming a core catalytic phase by slurry technique in such a manner that salts containing iron, nickel, D and E is dissolved in water, mixed with a solution containing silica sol and salt of molybdeum with the adjustment of the pH thereof to 2–5, and dried, followed by calcination at temperature of 200–700° C.; and (b) forming a shell catalytic phase in such a manner that the core catalytic phase as support is impregnated in a solution containing bismuth, A, B, and C, dried and calcined at temperature of 200–700° C.

This invention is explained in more detail as set forth hereunder.

In line with the chemical composition of the solid catalyst according to the invention, the core and shell catalytic phase thereof are described as $[(100-z) \%=D_dE_eFe_fNi_gMo_mO_y+z \% \ SiO_2]$ and $[B_{in}A_aB_bC_cO_x]$, respectively. However, it should be noted that the description of the catalyst in terms of a simple combination of the two phases as $[100-z) \% \ Bi_aA_aB_bC_cD_dE_eFe_fNi_gMo_mO_{x+y}+z \% \ SiO_2]$ may unduly simplify the invention herein. Therefore, the invention is explained by separating the core from the shell catalytic phase.

The core catalytic phase of the solid catalyst according to this invention is prepared by a "slurry technique" using silicon, and iron, nickel and molybdenum as main component, with or without the addition of D and E. More specifically, the slurry technique comprises the following steps: The silica sol, and salts containing dissociable anions (e.g., acetate, citrate, nitrate, and triphenyl) or the compounds thereof are mixed and removed of the solvent by heating or extraction to prepare a slurry. In the case of its further treatment, the pH of the resulting slurry is adjusted to 2–7, preferably 3–5 and dried or molded with spray dryer, followed by calcination at 200–700° C., preferably 280–500° C. The resultant is employed as support.

The shell catalytic phase is prepared as follows:

The salt solution containing a compound corresponding to $[Bi_nA_aB_bC_cO_x]$, whose main components are bismuth, A, B and C, is dissolved in an appropriate solvent, after which the core catalytic phase is impregnated into the salt solution. The salt solution containing the above mentioned anions (e.g., acetate, citrate, nitrate, and triphenyl) may be also employed in certain case.

The impregnation may be carried out in the form of mixture containing the components or individually. In the case of impregnating individually, it is preferred that the order of impregnation is C, B, A and Bi. In all cases, it is the most preferable that Bi is finally impregnated.

The impregnated material is dried at 50–200° C., preferably 100–130° C. and calcined again at 200° C.–700° C., thus obtaining a solid catalyst of this invention.

In line with the process of preparing a solid catalyst of this invention, the order of impregnation and temperature of calcination are pivot points and thus the conversion and selectivity of the prepared solid catalyst are drastically decreased, if the process dose not contain to the above condition.

This invention is on the basis of the fact that the core and shell catalytic phase is indispensable part with respect to the catalytic activity and each of the core and shell has different functions. Hence, when both phases have the components shown as in formula (1), the solid catalyst may achieve the maximum catalytic activity based on the synergy effects therein.

On the basis of comparison with catalyst prepared by sole slurry technique, it is expected that each of the components contained catalyst of this invention has different function view of the traditional theory.

In addition, the solid catalyst according to this invention has been proved to produce acrylonitrile with higher yield while using less amount of expensive bismuth which had been used as essential component of the conventional catalyst.

The following examples illustrate various aspects of this invention but are not be construed to limit the claims in any manner whatsoever.

PREPARATIVE EXAMPLE 1

Solution A was prepared by dissolving 18.66 g of $Fe(NO_3)_3 9H_2O$, and 39.33 g of $Ni(NO_3)_3 6H_2O$ in 10% $HNO_3$ solution(150 ml). Solution B was prepared in such a manner that after 29.12 g of $(NH_4)_6Mo_2O_{24} 9H_2O$ was dissolved in 240 ml of water by heating 40% silica sol (93.83 g) was added to the mixture. Solution A was added to solution B with stirring, following by adjusting pH to 3 with ammonia water. After evaporating the solvent by heating on a hot plate, the residue was dried in oven at 140° C., calcined again upon slow heating from 290° C. to 450° C., and pulverized to 25–70 mesh to obtain a catalyst having a chemical composition of $50\% MoFe_{0.28}Ni_{0.82}O_y + 50\% SiO_2$.

The reaction was carried out in fixed bed reactor under specific reaction conditions (temperature: 445° C., mole ratio of propylene/ammonia/oxygen/nitrogen: 1/1.3/2.2/9.6, contact time: 0.6 sec) in the presence of the catalyst, so prepared from the above. Propylene conversion was 8.2%, and selectivity to acrylonitrile was 42%.

PREPARATIVE EXAMPLE 2

Solution C was prepared by dissolving 2.33 g of $Fe(NO_3)_3 9H_2O$, and 4.92 g of $Ni(NO_3)_3 6H_2O$ in 10% $HNO_3$ (20 ml). Then, 3.64 g of $(NH_4)_6Mo_7O_{24} 4H_2O$ was dissolved in water, and 85% $H_3PO_4$ (0.071 g) and 40% silica sol (12.2 g) was added to the mixture with stirring, thereby preparing a homogeneous mixture. The solution C was added to the homogeneous mixture and its pH was adjusted to 3 with ammonia water. After evaporating the solvent by heating, the residue was dried at 140° C., calcined upon slow heating from 290° C. to 450° C., and pulverized to 27–70 mesh to obtain a catalyst having a chemical composition of $50\% MoFe0.25Ni_{0.82}Bi_{0.03}P_{0.03}O_y + 50\% SiO_2$.

The conversion of propylene was carried out as the Preparative example 1. Propylene conversion was 56.5%, and selectivity to acrylonitrile was 82.6%.

EXAMPLE 1

0.3 ml of $Bi(NO_3)_3 5H_2O$ solution (0.25 g/ml) was collected and stirred evenly with the addition of 10% $HNO_3$ solution. Then, 235 g of oxide—i.e. support-formed from the Preparative example 1 was impregnated with above solution dried at 120° C., and calcined at 575° C. for 3 hours to obtain a catalyst having a chemical composition of $[Bi_{0.03}O_x][50\% MoFe_{0.28}Ni_{0.82}O_y + 50\% SiO_2]$.

The conversion of propylene was carried out by the same procedure as described in the Preparative example 1. Propylene conversion was 71.9%, and selectivity to acrylonitrile was 85.8%.

EXAMPLE 2

The catalyst was prepared in the same procedure as described in the Example 1, except of the fact that the support was impregnated with 85% $H_3PO_4$ (0.071 g), dried and subsequently was impregnated with $Bi(NO_3)_3 5H_2O$, thereby preparing a catalyst having a chemical composition of $[Bi_{0.03}P_{0.03}O_x][50\% MoFe_{0.28}Ni_{0.82}O_y + 50\% SiO_2]$.

The conversion of propylene was carried out by the same procedure as described in the Preparative example 1. Propylene conversion was 80.1%, and selectivity to acrylonitrile was 86.1%.

EXAMPLE 3

The catalyst was prepared in the same procedure as described in the Example 1, except of the fact that the support was impregnated with $(NH_4)_6Mo_7O_{24} 4H_2O$, dried and subsequently was impregnated with $Bi(No_3)_2 5H_2O$ thereby preparing a catalyst having a chemical composition of $[Bi_{0.02}Mo_{0.03}O_2][50\% MoFe0.28Ni0.82O_y + 50\% SiO_2 \upsilon$.

The conversion of propylene was carried out by the same procedure as described in the Preparative example 1. Propylene conversion was 80.7%, and selectivity to acrylonitrile was 85.1%.

EXAMPLE 4

The catalyst was prepared in the same procedure as described in the Example 1, except of the fact that the support was prepared by using Co in place of partial Ni, and the catalyst having a chemical composition of $[Bi_{0.03}P_{0.03}O_x][50\% \ MoFe_{0.28}Ni_{0.66}Co_{0.16}O_y 50\% \ SiO_2]$ was finally prepared.

The conversion of propylene was carried out by the same procedure as described in the Preparative example 1. Propylene conversion was 76.4%, and selectivity to acrylonitrile was 86.7%.

The conversion of propylene was carried out by the same procedure as described in the Preparative example 1. Propylene conversion was 76.4%, and selectivity to acrylonitrile was 86.7%.

EXAMPLE 5

The catalyst was prepared in the same procedure as described in the Example 1, except of the fact that the support was prepared by using Mg in place of partial Ni, and the catalyst having a chemical composition of $[Bi_{0.03}P_{0.03}O_x][50\% \ MoFe_{0.28}Ni_{0.66}Mg_{0.16}O_y 50\% \ SiO_2]$ was finally prepared.

The conversion of propylene was carried out by the same procedure as described in the Preparative example 1. Propylene conversion was 82.2%, and selectivity to acrylonitrile was 85.8%.

EXAMPLE 6

The catalyst was prepared in the same procedure as described in the Example 1, except of the fact that the support was prepared by using Mn and Co in place of partial Ni, and the catalyst having a chemical composition of $[Bi_{0.03}P_{0.03}O_x][50\% \ MoFe_{0.28}Ni_{0.59}Mn_{0.07}Co_{0.06}O_y + 50\% \ SiO_2]$ was finally prepared.

The conversion of propylene was carried out by the same procedure as described in the Preparative example 1. Propylene conversion was 74.6%, and selectivity to acrylonitrile was 85.9%.

EXAMPLE 7

The catalyst was prepared in the same procedure as described in the Example 1, except of the fact that the support was prepared by using Co and Cr in place of partial Ni and Fe, respectively, and the catalyst having a chemical composition of $[Bi_{0.03}P_{0.03}O_x][50\% \ MoFe_{0.20}Ni_{0.70}Co_{0.12}Cr_{0.08}O_y + 50\% \ SiO_2]$ was finally prepared.

When the conversion of propylene was carried out by the same procedure as described in the Preparative example 1. Propylene conversion was 78.6%, and selectivity to acrylonitrile was 86.5%.

EXAMPLE 8

The catalyst was prepared in the same procedure as described in the Example 1, except of the fact that the support was prepared by using Co and Ce in place of partial Ni and Fe, respectively, and the catalyst having a chemical composition of $[Bi_{0.03}P_{0.03}O_x][50\% \ MoFe_{0.20}Ni_{0.20}Co_{0.12}Ce_{0.06}O_y 50\% \ SiO_2]$ was finally prepared.

The conversion of propylene was carried out by the same procedure as described in the Preparative example 1. Propylene conversion was 71.5%, and selectivity to acrylonitrile was 87.2%.

EXAMPLE 9

The catalyst was prepared in the same procedure as described in the Example 1, except of the fact that a impregnation was carried according to the following order. Mn, P and Bi. Finally, the catalyst having a chemical composition of $[Bi_{0.03}P_{0.03}Mn_{0.03}O_x][50\% \ MoFe_{0.28}Ni_{0.82}O_y + 50\% \ SiO_2]$ was prepared.

The conversion of propylene was carried out by the same procedure as described in the Preparative example 1. Propylene conversion was 82.2%, and selectivity to acrylonitrile was 85.4%.

EXAMPLE 10

The catalyst was prepared in the same procedure as described in the Example 1, except of the fact that an impregnation was carried according to the following order: Mg, P and Bi. Finally, the catalyst having a chemical composition of $[Bi_{0.03}P_{0.03}Mg_{0.02}O_x][50\% \ MoFe_{0.28}Ni_{0.82}O_y + 50\% \ SiO_2]$ was prepared.

The conversion of propylene was carried out by the same procedure as described in the Preparative example 1. Propylene conversion was 81.2%, and selectivity to acrylonitrile was 85.0%.

EXAMPLE 11

The catalyst was prepared in the same procedure as described in the Example 1, except of the fact that a impregnation was carried according to the following order: Fe, P and Bi. Finally, the catalyst having a chemical composition of $[Bi_{0.03}P_{0.03}Fe_{0.02}O_x][50\% \ MoFe_{0.28}Ni_{0.82}O_y + 50\% \ SiO_2]$ was prepared.

The conversion of propylene was carried out by the same procedure as described in the Preparative example 1. Propylene conversion was 80.3%, and selectivity to acrylonitrile was 86.1%.

EXAMPLE 12

The catalyst was prepared in the same procedure as described in the Example 1, except of the fact that a impregnation was carried according to the following order: Ce, P and Bi. Finally, the catalyst having a chemical composition of $[Bi_{0.03}P_{0.03}Ce_{0.02}O_x][50\% \ MoFe_{0.28}Ni_{0.82}O_y + 50\% \ SiO_2]$ was prepared.

The conversion of propylene was carried out by the same procedure as described in the Preparative example 1. Propylene conversion was 81.1%, and selectivity to acrylonitrile was 85.5%.

EXAMPLE 13

The catalyst was prepared in the same procedure as described in the Example 1, except of the fact that a impregnation was carried according to the following order: Ni, Te, P and Bi. Finally, the catalyst having a chemical composition of $[Bi_{0.03}P_{0.03}Ni_{0.02}Te_{0.01}O_x][50\% \ MoFe_{0.28}Ni_{0.82}O_y + 50\% \ SiO_2]$ was prepared.

The conversion of propylene was carried out by the same procedure was described in the Preparative example 1. Propylene conversion was 78.1%, and selectivity to acrylonitrile was 86.0%.

EXAMPLE 14

The catalyst was prepared in the same procedure as described in the Example 1, except of the fact that a impregnation was carried according to the following order: Ce, Cs, P and Bi. Finally, the catalyst having a chemical composition of $[Bi_{0.03}P_{0.03}Cs_{0.002}Ce_{0.02}O_x][50\% \ MoFe_{0.28}Ni_{0.82}O_y + 50\% \ SiO_2]$ was prepared.

The conversion of propylene was carried out by the same procedure was described in the Preparative example 1. Propylene conversion was 77.6%, and selectivity to acrylonitrile was 85.5%.

EXAMPLE 15

The catalyst was prepared in the same procedure as described in the Example 1, except of the fact that a spray dryer was used in a process of manufacturing a support so as to preparing the catalyst, which may be applied to fluidized bed reactor, and a impregnation was carried according to the following order: Ni, K, P and Bi. Finally, the catalyst having a chemical composition of $[Bi_{0.05}P_{0.05}K_{0.01}Ni_{0.03}O_x][50\%\ MoFe_{0.28}Ni_{0.82}O_y+50\%\ SiO_2]$ was prepared.

Then, ammoxidation of propylene was carried out in fluidized bed reactor manufactured with glass under specific reaction conditions (temperature: 445° C., mole ratio of propylene/ammonia/air: 1/1.1/11, contact time: 3 sec). Propylene conversion was 94.5%, and selectivity to acrylonitrile was 82.4%.

TABLE 1

| Category | Conversion of Propylene (%) | Selectivity of Acrylonitrile (%) |
| --- | --- | --- |
| Prep example 1 | 8.2 | 42.0 |
| Prep example 2 | 56.5 | 82.6 |
| Example 1 | 71.9 | 85.8 |
| Example 2 | 80.1 | 86.1 |
| Example 3 | 80.7 | 85.1 |
| Example 4 | 76.4 | 86.7 |
| Example 5 | 82.2 | 85.8 |
| Example 6 | 74.6 | 85.9 |
| Example 7 | 78.6 | 86.5 |
| Example 8 | 71.5 | 87.2 |
| Example 9 | 82.2 | 85.4 |
| Example 10 | 81.2 | 85.0 |
| Example 11 | 80.3 | 86.1 |
| Example 12 | 81.1 | 85.5 |
| Example 13 | 78.1 | 86.0 |
| Example 14 | 77.6 | 85.5 |
| Example 15 | 94.5 | 82.4 |

What is claimed is:

1. A solid catalyst comprising a core and shell catalytic phase for use in the manufacturing of a nitrile compound, wherein the solid catalyst is expressed by the following formula (1):

$$[Bi_nA_aB_bC_cO_x][(100-z)\%\ D_dE_eFe_fNi_gMo_mO_y+z\%\ SiO_2] \quad (1)$$

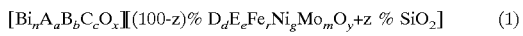

wherein:

A is one or more elements selected from the group consisting of boron, phosphorus, molybdenum and arsenic;

B is one or more elements having the atomic valence of 1–2 selected from the group consisting of potassium, cesium, nickel, cobalt, manganese and magnesium;

C is one or more elements having the atomic valence of 3–6 selected from the group consisting of iron, chromium, cerium, niobium, vanadium and tellurium;

D is one or more elements having the atomic valence of 3–6 selected from the group consisting of aluminum, cerium and chromium;

E is one or more elements having the atomic valence of 1–2 selected from the group consisting of cobalt, manganese, magnesium, calcium, copper and cesium;

when m is 1, n is 0,001–3, a is 0.001–3, b is 0–3, c is 0–1, d is 0–3, e is 0–3, f is 0.01–5, g is 0.01–5, and z is 0–90; and x and y are numbers such that the valence requirements of the other elements for oxygen in the core and shell catalytic phase, respectively are satisfied.

2. The solid catalyst according to claim 1, wherein the solid catalyst has a structure comprising the core catalytic phase with the chemical composition of $[(100-z)\%D_dE_eFe_fNi_gMo_mO_y+z\%SiO_2]$ and the shell catalytic phase with the chemical composition of $[Bi_nA_aB_bC_cO_x]$.

3. A method for producing a nitrile compound comprising reacting an olefin with ammonia under ammoxidation conditions in the presence of the solid catalyst of claim 1.

4. A process for preparing a solid catalyst expressed by the following formula (1):

$$[Bi_nA_aB_bC_cO_x][(100-z)\%D_dE_eFe_fNi_gMo_mO_y+z\%SiO_2] \quad (1)$$

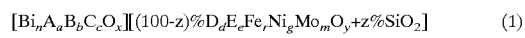

wherein:

A is one or more elements selected from the group consisting of boron, phosphorus, molybdenum and arsenic;

B is one or more elements having the atomic valence of 1–2 selected from the group consisting of potassium, cesium, nickel, cobalt, manganese and magnesium;

C is one or more elements having the atomic valence of 3–6 selected from the group consisting of iron, chromium, cerium, niobium, vanadium and tellurium;

D is one or more elements having the atomic valence of 3–6 selected from the group consisting of aluminum, cerium and chromium;

E is one or more elements having the atomic valence of 1–2 selected from the group consisting of cobalt, manganese, magnesium, calcium, copper and cesium;

when m is 1, n is 0.001–3, a is 0.001–3, b is 0–3, c is 0–1, d is 0–3, e is 0–3, f is 0.01–5, g is 0.01–5, and z is 0–90; and x and y are numbers such that the valence requirements of the other elements for oxygen in the core and shell catalytic phase, respectively, are satisfied, the process comprising the steps of:

(a) forming a core catalytic phase by slurry technique in such a manner that salts containing iron, nickel, D and E are dissolved in water, mixed with a solution containing silica sol and salt of molybdenum with the adjustment of the pH thereof to about 2 to about 7, then dried and molded, followed by calcination at temperature of about 200 to about 700° C.; and (b) forming a shell catalytic phase in such a manner that the core catalytic phase as support is impregnated with a solution containing bismuth, A, B and C, dried and calcined at temperature of 200–700° C.

5. The process of preparing a solid catalyst according to claim 4, wherein the impregnation is carried out in accordance with the following order: C, B, A and Bi.

* * * * *